United States Patent [19]

Casale et al.

[11] Patent Number: 5,276,181
[45] Date of Patent: Jan. 4, 1994

[54] CATALYTIC METHOD OF HYDROGENATING GLYCEROL

[76] Inventors: Bruno Casale, Via Scavini 25, 28100 Novara; Ana Maria Gomez, Via Compana 27, 10125 Torino, both of Italy

[21] Appl. No.: 911,146

[22] Filed: Jul. 9, 1992

[30] Foreign Application Priority Data

Jul. 10, 1991 [IT] Italy .............................. T09/A000539

[51] Int. Cl.$^5$ ....................... C07C 31/18; C07C 59/08
[52] U.S. Cl. ..................................... 562/589; 568/861
[58] Field of Search ......................... 568/861; 562/589

[56] References Cited

U.S. PATENT DOCUMENTS 4,430,253 2/1984 Dubeck et al. .
4,476,331 10/1984 Dubeck et al. ..................... 568/861
4,496,780 1/1985 Arena .

FOREIGN PATENT DOCUMENTS 0086296 7/1982 European Pat. Off. .
0072629 2/1983 European Pat. Off. .

OTHER PUBLICATIONS

C. Montassier, et al., "Acqueous polyol conversions on ruthenium and on sulfur-modified ruthenium", Journal of Molecular Catalysis, vol. 70, No. 1, 1991, pp. 99–110.
Montassier, C. et al., *Hetergeneous Catalysts and Fine Chemicals*, pp. 165–170 (Elsevier Science Publishers Publishers 1988).

*Primary Examiner*—Marianne M. Cintins
*Assistant Examiner*—Rebecca Cook

[57] ABSTRACT

A catalytic method of hydrogenating glycerol is directed essentially towards the production of oxygenated compounds having from 1 to 3 carbon atoms, particularly 1,2-propandiol and lactic acid. It provides for glycerol to be placed in contact with hydrogen and made to react therewith in the presence of a ruthenium catalyst modified with sulphides and of a base, at a temperature of at least 200° C.

8 Claims, No Drawings

CATALYTIC METHOD OF HYDROGENATING GLYCEROL

DESCRIPTION

The present invention relates to a catalytic method of hydrogenating glycerol, particularly in order to produce industrially useful oxygenated compounds of greater commercial value.

The saponification and transesterification of fats in order to produce fatty acids and methyl esters thereof lead to the production of large quantities of impure glycerol which is normally considered to be a byproduct since it requires expensive purification processes in order to be used further or sold.

On the other hand, the known methods of converting purified glycerols by hydrogenation are unattractive from an industrial point of view.

A catalytic method of hydrogenating glycerol is described by Montassier et al in "Heterogeneous catalysis and fine chemicals", Elsevier Science Publishers, 1988, pages 165–170. According to this article, the hydrogenation of glycerol with a ruthenium catalyst supported on silica at 240° C. with a hydrogen pressure of 10 MPa leads to the formation of gaseous hydrocarbons, mainly methane, and of 1,2-propandiol, ethandiol and 1-propanol. On the basis of these results, the authors conclude that ruthenium shows no significant selectivity in the competitive hydrogenolysis of C—C and C—O bonds and report that the same behavior in terms of selectivity is obtained with Raney nickel, rhodium and iridium catalysts. This method is therefore unsuitable for industrial use because considerable quantities of gaseous hydrocarbon compounds are formed, while selectivity towards the formation of oxygenated compounds, such as, for example, 1,2-propandiol and ethandiol, is low.

German patent DE-PS-541362 describes the hydrogenation of glycerol with a nickel catalyst to form 1,2-propandiol. Tests carried out by the Applicant have shown that, even with the use of nickel as the catalyst, high yields of glycerol conversion can be achieved only at high temperatures of about 270° C., at which temperatures large quantities of unwanted gaseous hydrocarbons, mainly methane, are produced.

U.S. Pat. No. 4,476,331 describes a two-stage method of hydrogenating carbohydrates, particularly glucose, in which a ruthenium catalyst modified with sulphides is used during the second stage for the hydrogenation of sorbitol to produce mainly ethylene and propylene glycols and glycerol.

The object of the present invention is to provide a method which enables glycerol, particularly impure glycerol produced as a byproduct of processes for the saponification and transesterification of fats, to be converted with a high conversion rate and good overall selectivity towards the production of oxygenated compounds. Within the scope of the present invention, it has been discovered that this object is achieved by the hydrogenation of glycerol with the use of a ruthenium catalyst, the activity of which is moderated by sulfides, in the presence of a base.

The subject of the present invention is therefore a catalytic method of hydrogenating glycerol in order to produce mainly oxygenated compounds having from 1 to 3 carbon atoms, characterized in that the glycerol is placed in contact with hydrogen and made to react therewith in the presence of a ruthenium catalyst modified with sulfides, and of a base, at a temperature of at least 200° C.

It has been found that, with these process conditions, the reaction product is constituted by a mixture consisting essentially of a predominant quantity of 1,2-propandiol, with lactic acid and ethylene glycol, the remainder being constituted by methanol, ethanol and/or propanol and unreacted glycerol. The production of considerable quantities of lactic acid, the formation of which involves both an oxidation and a reduction at different sites on the glycerol molecule, constitutes a particularly surprising characteristic of the method of the invention. Moreover, lactic acid, the production of which as a hydrogenation product of glycerol is not described in the literature, can easily be separated from the other components of the reaction product.

The method of the invention may be carried out with glycerol resulting directly from the saponification and transesterification of fats, without the need to subject it to intermediate purification processes, and the process can therefore be integrated within a process for processing fats, to produce industrially useful final products of a high commercial value.

The ruthenium catalyst used may be a commercial catalyst supported on an inert substrate, preferably granular activated carbon, and the concentration of ruthenium on the substrate is typically between 0.5 and 7% by weight., The catalyst may be modified with sulfides beforehand during its preparation, or in situ by the addition of a compound which acts as a source of sulfur. For this purpose, preferred sulfurated compounds are sodium sulfide, bisulfates, particularly of sodium bisulfates, and thiosulfates. The ratio of sulfur ions to ruthenium is generally between about 0.2 and about 5 moles of sulfur ions per mole of ruthenium, preferred ratios being between 0.5 and 2.

As will become clear from the following experimental data, it has been found necessary to use a basic promoter in order to achieve high overall yields of glycerol conversion. In the absence of the promoter, adequate overall selectivity towards the desired oxygenated products is nevertheless achieved, but the overall glycerol-conversion rate is unsatisfactory. The quantity of the basic promoter used is between 10 and 45% of the quantity of glycerol in moles and is sufficient to bring the pH within the basic range of from 8 to 13 and, preferably, between 11 and 12.5. The preferred bases are hydroxides of alkali metals or alkaline-earth metals, particularly sodium and calcium hydroxides, and salts with basic reactions, such as sodium carbonate and quarternary ammonium salts.

The operative conditions required for the reaction are a reaction temperature higher than 200° C., preferably of between 220 and 280° C., and a total pressure between 5 and 20 MPa, preferably of between 10 and 15 MPa. In the case of batch reactions, the concentration of the metal catalyst is generally between about 2% and 0.05 of the weight of the glycerol (preferably from 1 to 0.25%). The concentration of the basic substance is generally within the range of from 0.2 to 1.5 moles per mole of glycerol.

The glycerol is preferably supplied to the hydrogenation reactor in aqueous solution at concentrations generally of between 10 and 60% by weight, preferably of from 30 to 40% by weight.

It is also possible, however, to use nonaqueous solvents in which glycerol is at least partially soluble, under the reaction conditions, and which do not interfere with the hydrogenation reaction. These solvents include polar solvents, particularly alcohols such as methanol, ethanol and propanol. If the reaction is carried out in an alcoholic solvent, the basic promoter is preferably the corresponding alkali metal or alkaline-earth metal alkoxide.

The invention will now be described in greater detail on the basis of Examples 1 to 8, of which Examples 1, 2, 5 and 6 are comparative examples and Examples 3, 4, 7 and 8 illustrate embodiments of the invention.

EXAMPLES 1–8

Experimental tests were carried out discontinuously using, as the reactor, a 500 cm³ Brignole autoclave with a magnetic stirring system having a stirrer with four radial blades and four washplates.

The catalyst used was ruthenium supported on granular activated carbon of a type commonly available on the market, the average granule size of the catalyst being about 2 mm and the ratio of ruthenium to the substrate being 5% by weight. The quantity of catalyst used was such that the ratio of ruthenium to glycerol was 0.4% by weight.

The method of operation was as follows. The autoclave was loaded with about 250 cm³ of an aqueous solution of glycerol at a concentration of 30% by weight with the desired quantity of the catalyst and, when used, of the basic promoter. The autoclave was then closed and flushed with hydrogen several times to eliminate all the air present and then pressurized with hydrogen at 130 bars, heated to the desired reaction temperature, and kept under these conditions for two hours. At the end of this period, the autoclave was cooled to ambient temperature and a gas sample was withdrawn under these conditions. The autoclave was then brought to atmospheric pressure and opened to enable the reaction liquid to be discharged, weighed, filtered to separate the catalyst, and analyzed.

The liquid was analyzed by high-performance liquid chromatography (HPLC) in a Waters chromatograph (Model 411) with an Aminex HPX 87H column and a refractive index detector.

The gas, on the other hand, was analyzed by gas chromatography in a Carlo Erba Fractovap Model C-ATC/F chromatograph with a silica gel column, operating at 50° C. with a thermal conductivity detector.

The following table gives the process conditions used in the tests carried out, as regards the temperature, the molar ratio between the sulfur and the ruthenium, and the concentration of sodium hydroxide in the solution, and gives the results obtained. In the results, the conversion rate is expressed as the ratio, in percentage terms, between the glycerol converted and the glycerol supplied, and the selectivity towards the various reaction products is expressed as the ratio, in percentage terms, between the glycerol converted into the product under consideration and the total glycerol converted. Due to inevitable experimental and analytical errors, the sums of the selectivities towards the various products do not give values of 100, but give slightly higher or lower values.

The symbols used in the table below, have the following meanings:
PG: 1,2 propandiol
EG: 1,2 ethandiol
AL: lactic acid
MeOH: methanol
EtOH: ethanol
iPrOH: iso-propanol
Gas: $CH_4 + CO + CO_2$

| Example NO. | T° (°C.) | S/RU (mol/mol) | Na(OH) (g/l) | Conversion (%) | Selectivity % | | | | | | |
|---|---|---|---|---|---|---|---|---|---|---|---|
| | | | | | EG | PG | AL | MEOH | ETOH | iPrOH | GAS |
| 1 | 240 | — | — | 48 | 18.6 | 24.5 | 1.9 | 2.3 | 0.7 | 0.9 | 46.5 |
| 2 | 240 | 1 | — | 6 | 6.4 | 52.6 | 15 | — | — | — | 1.1 |
| 3 | 240 | 1 | 23 | 100 | 5.1 | 75.2 | 13.4 | — | 0.6 | 2 | 0.01 |
| 4 | 270 | — | — | 82 | 6.7 | 20.5 | 1.5 | 1.2 | 1.5 | 0.9 | 43 |
| 5 | 270 | 1 | — | 13 | 2.5 | 41.6 | 9 | 3 | 1.5 | 7.4 | 2 |
| 6 | 270 | 1 | 23 | 99.9 | 5.2 | 50.4 | 13.6 | 4 | 2 | 6.6 | 0.6 |
| 7 | 270 | 1 | 46 | 100 | 3.6 | 31.3 | 23.5 | 5 | 1.7 | 6 | 0.6 |
| 8 | 240 | 1 | 46 | 100 | 4.7 | 52.2 | 18.3 | 2.1 | 3 | 2.8 | 0.05 |

A comparison of tests 1 and 4, which were carried out without the addition of an additive to the glycerol solution, shows that an increase in the reaction temperature from 240° C. to 270° C. substantially increases the conversion rate. The selectivity towards the desired products is unsatisfactory in both cases, however, because large quantities of gaseous products, mainly methane, are formed.

The addition of sodium sulfide nonhydrate to the glycerol solutions (Examples 2 and 5) achieves better selectivity values and the formation of gaseous products is greatly reduced. The overall conversion rate, however, is very low in this case.

If sodium hydroxide is also added to the glycerol solution (Examples 3, 6, 7 and 8), practically complete conversion is achieved and the selectivity remains satisfactory, as in the previous case.

In this connection, it should be noted that an increase in the concentration of sodium hydroxide increases selectivity towards lactic acid (Example 7). A smaller quantity of sodium hydroxide, on the other hand, increases selectivity towards 1,2-propandiol.

Tests 1–7 were carried out with the use of glycerol having the purity of a reagent, whereas test 8 was carried out with glycerol resulting from the saponification of fats, without previous purification. The conversion and selectivity results of this test confirm the activity of the catalyst even in the presence of impure glycerol.

What is claimed is:
1. A catalytic method comprising hydrogenating glycerol to produce a product comprising 1,2-propandiol and lactic acid comprising the step of reacting the glycerol with hydrogen in the presence of a ruthenium catalyst and a base at a temperature of at least 200° C. and at a total pressure of from 5 to 20 Mpa, wherein:
   a) the ruthenium catalyst is used in the presence of sulfide ions, wherein the ratio of sulfide ions to ruthenium in the catalyst is between 0.2 and 5 moles of sulfur ions per mole of ruthenium; and b) the base is a compound selected from the group consisting of hydroxides of alkali metals, hydroxides of alkaline-earth metals, sodium carbonate, and quaternary ammonium salts and is used in a quantity to bring the pH within the basic range of from 8 to 13.

2. A method according to claim 1, wherein the ruthenium catalyst is supported on an activated carbon substrate, with a percentage of ruthenium on the substrate of between 0.5 and 7%.

3. A method according to claim 1, wherein the ratio of sulfide ions to ruthenium in the catalyst is between 0.5 and 2.

4. A method according to claim 1, wherein the glycerol is supplied in aqueous solution at a concentration of from 10 to 60% by weight.

5. A method according to claim 1, wherein the quantity of the base used is from 10 to 45% of the quantity of glycerol in moles.

6. A method according to claim 1, wherein the reaction is carried out at a temperature of between 200 and 280° C., with a total pressure of from 10 to 15 MPa.

7. A method according to claim 6, wherein the reaction temperature is between 220 and 280° C.

8. A method according to claim 1, wherein the glycerol used is impure glycerol resulting from the saponification or transesterification of fats, without previous purification.

* * * * *

UNITED STATES PATENT AND TRADEMARK OFFICE
CERTIFICATE OF CORRECTION

PATENT NO. : 5,276,181
DATED : January 4, 1994
INVENTOR(S) : Bruno Casale, Ana Maria Gomez It is certified that error appears in the above-indentified patent and that said Letters Patent is hereby corrected as shown below:

On the Title Page, Item [30] under Foreign Application Priority Data: change "T09/A000539" to --T091A000539--.

Signed and Sealed this

Second Day of August, 1994

Attest:

BRUCE LEHMAN

Attesting Officer      Commissioner of Patents and Trademarks